(12) United States Patent
Chu et al.

(10) Patent No.: US 6,190,918 B1
(45) Date of Patent: Feb. 20, 2001

(54) ANALYTE DETECTION DEVICE AND PROCESS

(75) Inventors: Amy H. Chu; Michael J. Wilcox, both of Elkhart, IN (US)

(73) Assignee: Bayer Corporation, Elkhart, IN (US)

( * ) Notice: Under 35 U.S.C. 154(b), the term of this patent shall be extended for 0 days.

(21) Appl. No.: 08/400,786

(22) Filed: Mar. 6, 1995

Related U.S. Application Data

(63) Continuation of application No. 08/102,296, filed on Aug. 5, 1993, now abandoned.

(51) Int. Cl.[7] ............................. G01N 33/48; G01N 21/00
(52) U.S. Cl. ................................. 436/63; 422/56; 422/57; 435/14; 435/22; 435/26; 436/71; 436/95; 436/166; 436/169; 436/170; 436/177
(58) Field of Search ................................. 422/56, 57, 61; 435/14, 22, 26; 436/71, 95, 63, 166, 169, 170, 177

(56) References Cited

U.S. PATENT DOCUMENTS

| | | | |
|---|---|---|---|
| 3,964,974 | * 6/1976 | Banauch et al. | 435/14 X |
| 4,066,512 | * 1/1978 | Lai et al. | 435/14 X |
| 4,181,500 | * 1/1980 | Cowsar et al. | 422/56 X |
| 4,186,251 | * 1/1980 | Tarbutton | 435/11 |
| 4,223,090 | * 9/1980 | Mazza | 435/26 X |
| 4,230,757 | * 10/1980 | Toner | 422/56 |
| 4,551,427 | * 11/1985 | Draeger et al. | 435/14 |
| 4,680,259 | * 7/1987 | Cumbo et al. | 422/56 X |
| 4,772,561 | * 9/1988 | Genshaw | 436/169 |
| 4,885,240 | * 12/1989 | Wu | 436/169 X |
| 4,898,813 | * 2/1990 | Albarella et al. | 422/56 X |
| 4,933,092 | * 6/1990 | Aunet et al. | 436/177 X |
| 5,116,763 | * 5/1992 | Greene et al. | 422/56 X |
| 5,135,716 | * 8/1992 | Thakore | 427/56 |
| 5,160,436 | * 11/1992 | Hildenbrand et al. | 422/56 X |
| 5,213,966 | * 5/1993 | Vuorinen et al. | 435/14 |
| 5,262,067 | * 11/1993 | Wilk et al. | 422/56 X |

FOREIGN PATENT DOCUMENTS

| | | |
|---|---|---|
| 535485 | * 4/1993 | (EP) . |
| 62-247259 | * 10/1987 | (JP) . |

OTHER PUBLICATIONS

R.K. Yamazaki et al. *Biochim. Biophys. Acta* 1970, 197, 90–92.*
H.J. Mersmann et al. *J. Anim. Sci.* 1987, 64, 148–164.*

* cited by examiner

*Primary Examiner*—Arlen Soderquist
(74) *Attorney, Agent, or Firm*—Roger N. Coe; Jerome L. Jeffers

(57) ABSTRACT

The present invention provides a device and a process for detecting an analyte in a biological fluid. The device comprises a separating matrix for separating analyte from the fluid and means for detecting the analyte, where the separating matrix contains HEPES buffer, preferably in an amount between 70 and 150 millimolar. The process comprises applying the sample to the device having a separating matrix and then detecting analyte in the sample using the detection means. The presence of HEPES in the separation layer shortened the detection time.

15 Claims, 2 Drawing Sheets

ANALYTE DETECTION DEVICE AND PROCESS

This is a continuation, of application Ser. No. 08/102,296, filed Aug. 5, 1993, now abandoned.

FIELD OF THE INVENTION

The present invention relates to a device and a process for detecting an analytes in a biological fluid. A device comprises a separating matrix for separating an analyte from a sample fluid, where the separating matrix contains HEPES buffer. A process comprises applying a sample fluid to a device having a separating matrix and then detecting an analyte in the sample using detection means in a detection layer adjacent to the separating matrix.

DESCRIPTION OF THE BACKGROUND ART

There is a need in the end point detection art for devices and methods that allow for the rapid, accurate determination of analyte (e.g., glucose, triglyceride, cholesterol, etc.) concentration in very small sample volumes of biological fluid. The need for a device using small sample volumes is particularly relevant to the detection of blood glucose because of the difficulty and inconvenience of obtaining blood samples from subjects.

Currently available such devices include ACCUCHEK EASY TEST STRIPS™ and ACCUTREND® (Boehringer Mannheim Corp.). Those devices are multilayer reagent systems characterized by the absence of a buffering agent in the separation or filtration layer.

Buffer is commonly added to the composition present in a detection layer for the purpose of controlling the pH of the reagent composition present in said layer. The use of buffers for this purpose is described, for example, in U.S. Pat. No. 5,116,763.

The present invention provides a detection device having a HEPES-impregnated separation matrix, which HEPES serves to reduce the time needed for analyte detection. Unexpectedly, HEPES speeds up the end point determination in the detection layer. Other buffers do not demonstrate the same benefit.

BRIEF SUMMARY OF THE INVENTION

In one aspect, the present invention contemplates a device for detecting an analyte in a biological fluid sample, which device comprises:

a) a separation matrix containing HEPES; and
b) means for detecting an analyte, which detection means is vertically adjacent to the separation matrix and substantially coincident with that matrix such that analyte can move from the separation matrix to the detection means.

The amount of HEPES present is between 70 and 150 millimolar and preferably between 80 and 100 millimolar.

A detection means is preferably a matrix containing chemical reagents that interact with the analyte to generate a detectable signal. A preferred detection means for glucose is a synthetic membrane containing ATP, NAD, hexokinase, glucose-6-phosphate dehydrogenase, diaphorase and an indicator.

In a preferred embodiment, the separation matrix is a glass fiber filter. More preferably, the glass fiber filter has a sample application side adjacent to the cover portion and a reagent side adjacent to the detection means, whereby the glass fibers at the reagent side are shorter than the glass fibers at the application side.

The separation matrix can contain an aggregation-promoting substance that promotes aggregation of colloidal particles or cells or a surface active agent such as a non-hemolytic surfactant.

Preferably, the biological fluid is extracellular fluid and, more preferably, the fluid is blood.

A detection device can further comprise (1) a base portion having a transparent window, which base portion is situated such that the detection means is vertically adjacent to the base portion and at least partially coincident with the transparent window and (2) a cover portion having an aperture, which cover portion is vertically adjacent to the separation matrix.

Preferably, the transparent window in the base portion is made of glass or plastic such as polycarbonate.

In a preferred aspect, therefore, the present invention contemplates a device for detecting glucose in a biological fluid, which device comprises:

a) a plastic base portion having a polycarbonate clear window:
b) means for detecting glucose vertically adjacent to the base portion and at least partially coincident with the window, which detection means comprises a matrix containing ATP, NAD, hexokinase, glucose-6-phosphate dehydrogenase, diaphorase and an indicator;
c) a separation matrix containing HEPES vertically adjacent to the detection means and substantially coincident with that detection means; and
d) a cover portion having an aperture, which cover portion is vertically adjacent to the separation matrix and which aperture is coincident with the separation matrix.

In yet another preferred aspect, the present invention contemplates a process of detecting an analyte in a biological fluid, which process comprises the steps of:

a) providing an analyte detection device comprising:
  i) a separation matrix containing HEPES; and
  ii) means for detecting the analyte, which detection means is vertically adjacent to the separation matrix and substantially coincident with that matrix such that analyte can move from the separation matrix to the detection means;
b) applying a sample of the biological fluid to the separation matrix of the detection device;
c) maintaining the detection device for a time period sufficient for analyte to traverse the separation matrix, enter the detection matrix and for generation of a signal indicative of the presence of analyte; and
d) detecting the signal and thereby the presence of analyte.

In another preferred embodiment, the biological fluid is blood and the separation matrix contains an aggregation-promoting substance and a surface acting agent.

BRIEF DESCRIPTION OF THE DRAWINGS

In the drawings which form a portion of the specification.

DESCRIPTION OF THE INVENTION

I. Detection Device

Figure 1:
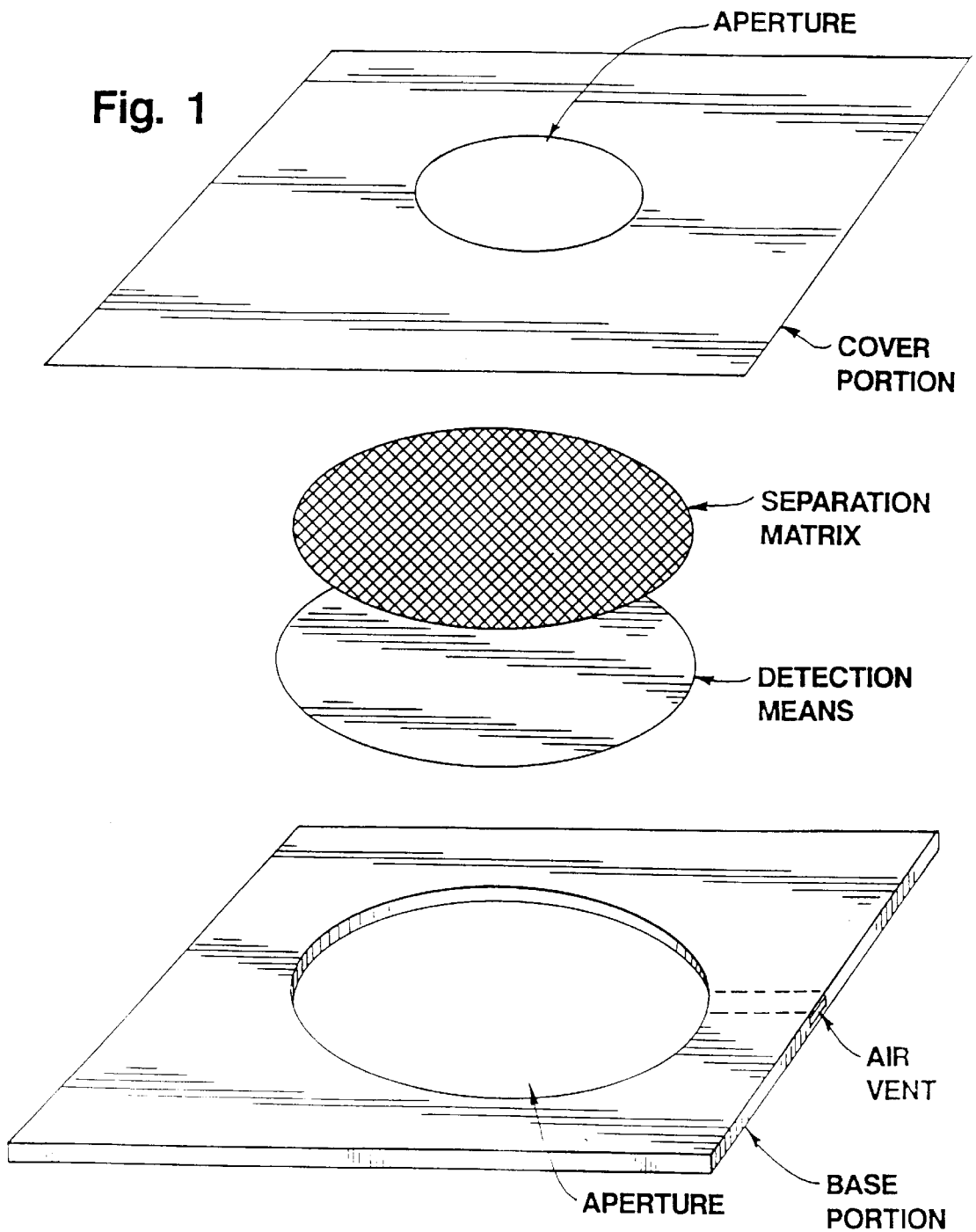
FIG. 1 shows a schematic representation of a detection device.

A device of the present invention is a multilayer reagent system device for detection of analyte in a biological fluid. Such a device comprises two layers situated vertically adjacent to one another (e.g., one layer is above the other).

A first layer serves at least to receive a sample of the biological fluid suspected of containing analyte and to separate analyte from other substances in the sample that interfere with analyte detection. As used herein, the phrase "separation matrix" means a layer that receives the sample and performs the separation function. As set forth hereinafter, a separation layer can serve other functions such as pretreatment of the sample.

A second layer receives analyte from the separation matrix and serves at least to detect analyte. As used herein, the word "detect" or its grammatical equivalents means measuring analyte and generating a detectable signal indicative of the presence of analyte. Preferably, such a generated signal is proportional to the amount or concentration of analyte in the sample of fluid. A detectable signal is a signal that is capable of detection by physical, chemical or other means. As used herein, the phrase "means for detecting" or its grammatical equivalents refers to a layer that serves at least that detection function.

In one preferred aspect, the present invention contemplates a device for detecting glucose in a biological fluid sample, which device comprises a separation matrix and a means for detecting glucose. A separation matrix used in a device of the present invention contains the buffer 4-(2-hydroxyethyl)-1-piperazine-ethanesulfonic acid (HEPES). In accordance with this preferred aspect, the present invention contemplates a glucose detection device comprising:

a) means for detecting glucose; and
b) a separation matrix containing HEPES, which matrix is vertically adjacent to the detection means and substantially coincident with that detection means such that glucose can move from the separation matrix to the detection means.

As used herein, the phrase "substantially coincident" means that the degree of overlap between vertically adjacent structures is greater than about fifty percent, preferably greater than about 75 percent and, more preferably greater than about 90 percent. As used herein, the term "matrix" indicates a substance that encloses, contains or embeds another substance.

In one embodiment, means for detecting an analyte comprises a matrix that contains chemical reagents used to detect glucose. That matrix is referred to herein as a detection matrix. A detection matrix is preferably a membrane fabricated of natural or synthetic material. Such membrane material is (1) chemically-resistant to a sample being analyzed (including the analyte and constituents of that sample) and to other reagents used in the device (e.g., means for detecting analyte) and (2) non-reactive (i.e., chemically-inert) with respect to all constituents of a sample being analyzed as well as to other components of the device. Preferably, a membrane used as a detection matrix is fabricated of synthetic material such as those set forth below in Table 1.

TABLE 1

| Source | Trade Name | Type | Membrane Charge | Pore Sizes (microns) |
|---|---|---|---|---|
| PALL | Biodyne A | Nylon | Zwitterion | 0.2, 0.45, 0.65, 1.2 and 3.0 |
|  | Biodyne B | Nylon | positive charged | 0.2, 0.45, 1.2 and 3.0 |
|  | Biodyne C | Nylon | negative charged | 0.2, 0.45, 1.2 and 3.0 |
|  | Loprodyne | Nylon | noncharged | 0.2, 0.45, 1.2 and 3.0 |
| S & S | Nylon 66 | Nylon | noncharged | 0.45 and 0.65 |
|  | Nytran | Nylon | positive charged | 0.45 and 0.65 |
|  | Optibind | Nitrocellulose | noncharged | 0.45 |
|  | Plastic Backing | Nitrocellulose | noncharged | 0.45 |
| CUNO | Zeta Bind | Nylon | noncharged | 0.45 and 0.65 |
|  | Zeta Bind | Nylon | positive charged | 0.45 |
| MSI | Magnagraph | Nylon | positive | 0.45 and 0.65 |
|  | Magna | Nylon | noncharged | 0.45 and 0.65 |
| MILLI-PORE | Duropore | Polyvinyl-idene Fluoride | noncharged | 0.65 |
| GELMAN | Versapor | Acrylic copolymer | noncharged | 0.2 and 0.45 |
|  | AP450 | Acrylic copolymer | noncharged | 0.45 |
|  | Thermapor | Poly-sulfone | noncharged | 0.8 |
|  | Ultrabind | Affinity Binding | noncharged | 0.45 |
| MEMTEC | Filterite | Poly-sulfone | asymmetric pore | 0.2 |
|  | Memtest | Affinity Binding | noncharged | 0.8 |

A detection means is preferably of low porosity. Preferred pore sizes are from about 0.2 microns to about 3.0 microns and, more preferably from about 0.45 to about 0.65 microns.

Preferably, means for detecting an analyte comprises one or more chemical reagents that interact with that analyte and generate a physical or chemical signal that is indicative of analyte presence. Preferably, a signal generated is proportional to the amount or concentration of analyte in the sample.

Chemical reagents used for detecting analytes are well known in the art. In a preferred embodiment, such chemical reagents interact with analyte to generate a change in color (e.g., a colorimetric assay of analyte). In a preferred embodiment, where the analyte is glucose, chemical reagents used for the colorimetric detection of glucose are those used in the well known hexokinase reaction. The chemical reactions and reagents involved in that reaction are set forth below.

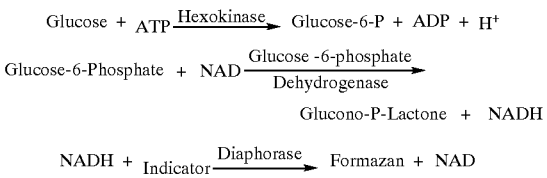

$$\text{Glucose} + \text{ATP} \xrightarrow{\text{Hexokinase}} \text{Glucose-6-P} + \text{ADP} + \text{H}^+$$

$$\text{Glucose-6-Phosphate} + \text{NAD} \xrightarrow{\text{Glucose-6-phosphate Dehydrogenase}} \text{Glucono-P-Lactone} + \text{NADH}$$

$$\text{NADH} + \text{Indicator} \xrightarrow{\text{Diaphorase}} \text{Formazan} + \text{NAD}$$

In accordance with that embodiment, a device of the present invention comprises a detection matrix that contains the substrates, enzymes and indicators needed for the hexokinase detection of glucose. Those reagents comprise adenosine triphosphate (ATP), nicotinamide adenine dinucleotide (NAD), hexokinase, glucose-6-phosphate dehydrogenase, diaphorase and an indicator. A preferred indicator is a tetrazolium salt such as 2-(p-Iodo-phenyl) -3-(p-nitrophenyl)-5-phenyltetrazolium chloride (i.e., INT), p-Nitro Blue Tetrazolium chloride (i.e., NBT) or 2-(4-difluoromethyl-5-chlorothiazolyl)-3-(3,4,5-trimethoxyphenyl)-5-(3,4-methylenedioxyphenyl) tetrazolium benzenesulfonate.

In other preferred embodiments, an analyte is cholesterol, triglyceride, amylase and the like. Chemical reagents used in the detection of those analytes are well known in the art. Exemplary such reagents are set forth hereinafter in Example 3.

A device of the present invention comprises a separation matrix vertically adjacent to a means for detecting analyte and substantially coincident to that detection means such that analyte can move from the separation matrix to the detection means. In a preferred embodiment, the separation matrix is in contact with the detection means.

Preferably, a separation matrix is a membrane filter fabricated of natural or synthetic chemically-resistant and chemically-inert materials as those terms are defined above. Preferably a separation matrix is highly porous to allow for movement of an analyte containing sample across the membrane filter and into a detection matrix. In an especially preferred embodiment, the separation matrix is a glass fiber filter. Porous glass fiber filters are commercially available (Whatman Ltd., England).

Where aligned vertically adjacent to a detection means in a device of the present invention, a separation matrix can be seen to have a sample application side directed away from the detection means and a reagent side directed toward and adjacent to the detection means. In a preferred embodiment, a separation matrix is heterogeneous with respect to those sides.

In a preferred embodiment, those sides are heterogeneous with respect to their ability to promote lateral spreading of a liquid sample applied to the matrix. According to this embodiment, the application side of a separation matrix promotes lateral spreading of an applied liquid sample to a lessor extent than the reagent side. Thus, spreading of an applied sample occurs as that sample traverses (passes through) a separation matrix from the application side to the reagent side and toward the detection means.

Where a separation matrix is a glass fiber filter, such a heterogeneous promotion of lateral spreading is accomplished by having the glass fibers at the reagent side shorter than the glass fibers at the application side. The use of such a heterogeneous glass fiber filter reduces the amount of sample needed for detection of an analyte in that sample and reduces the time need for such detection.

A separation matrix can further contain a substance that interacts with an applied sample so long as that substance does not adversely affect detection of an analyte. An exemplary such substance is an agent that promotes aggregation of colloidal particles or cells and serve to enhance separation of an analyte from other substances that likely interfere with analyte detection.

By way of example, where a biological fluid is blood, and means for detecting glucose is a calorimetric means, the presence of red blood cells would likely interfere with color detection. Red blood cells can be aggregated in a separation matrix such that those cells do not migrate to a detection means and interfere with color detection. A preferred aggregation-promoting substance for use with whole blood samples is an agglutination-promoting agent such as a lectin. A preferred lectin is potato lectin.

A separation matrix can also comprise a surface active agent such as a surfactant. Where a sample is whole blood, a preferred surfactant is a non-hemolytic surfactant such as a functionalized derivative of polyoxyethylene (e.g., Cremophor EL, Sigma Chem. Co., St. Louis, Mo.) or Surfynol 465 (Air Products and Chemicals, Inc.).

Preferably, a biological fluid is extracellular fluid such as blood, plasma, serum, urine and the like. A preferred extracellular fluid is blood.

In another embodiment of a device of the present invention, a separation matrix and a detection means are sandwiched between additional layers that serve to support the separation matrix and detection means, allow access to the device for sample application and permit detection of a generated signal.

In accordance with such a preferred embodiment, the present invention contemplates a device for detecting an analyte in a biological fluid, which device comprises:

a) a base portion having a transparent window:

b) means for detecting the analyte vertically adjacent to the base portion and at least partially coincident with that window:

c) a separation matrix containing HEPES, which separation matrix is vertically adjacent to the detection means and substantially coincident with that detection means such that analyte can move from the separation matrix to the detection means; and d) a cover portion vertically adjacent to the separation matrix, which cover portion has an aperture that is coincident with the separation matrix.

A base portion and a cover portion of a device of the present invention can be fabricated of any material that is chemically-resistant and chemically-inert as those terms are defined above.

Exemplary chemically-resistant and inert materials include glass, plastic and metal. A preferred material is a plastic such as polystyrene. Means for fabricating materials into a base or cover portion of suitable shape and size are well known in the art (See Examples, hereinafter).

A base portion contains an aperture that provides access to a detection matrix. Such access is needed for visualization or otherwise detection of a signal generated from an interaction between analyte and a chemical reagent used for detecting analyte.

In a preferred embodiment, an aperture in a base portion is covered with a transparent material that permits visualization of a generated signal. A transparent material used as a cover is fabricated of a chemically-resistant and chemically-inert substance as set forth above. A preferred transparent material is a transparent plastic such as polycarbonate.

At least a portion of the detection means is aligned coincident to an aperture in the base portion to allow for visualization of the generated signal through the base portion.

A cover portion has an aperture that is coincident with the separation matrix. A sample of biological fluid is applied to the separation matrix through the aperture in the cover portion.

II. A Process of Detecting Analyte in a Biological Fluid

In another aspect, the present invention contemplates a process for detecting an analyte in a biological fluid. In accordance with such a process, a sample of a biological fluid is applied to a separation matrix of a detection device comprising:

a) a separation matrix containing HEPES; and b) means for detecting analyte, which detection means is vertically adjacent to the separation matrix and substantially coincident with that matrix such that analyte can move from the separation matrix to the means for detecting analyte.

The device with the applied sample is then maintained at a temperature and for a period of time sufficient for analyte in the sample to traverse the separation matrix, enter the detection means, interact with the detecting means and generate a detectable signal indicative of analyte presence or proportional to the amount or concentration of analyte present. The generated signal is then detected through the transparent window in the base portion.

The device with the sample applied thereto is preferably maintained at a temperature of from about 4° C. to about 50° C., more preferably from about 15° C. to about 30° C. and, even more preferably at about 25° C..

In a preferred embodiment, maintenance time is less than about two minutes, and more preferably less than about one minute. Preferably, the sample is applied to the device in a volume of from about 5 microliter ($\mu$l) to about 20 $\mu$l, more preferably from about 3 $\mu$l to about 15 $\mu$l and, even more preferably from about 3 $\mu$l to about 10 $\mu$l.

In a preferred embodiment, the separation matrix is a glass fiber filter. That filter can further be impregnated with an aggregating-promoting substance such as a lectin and a surface acting agent such as a non-hemolytic surfactant.

A separation matrix and means for detecting analyte are preferably the same as set forth above. A device used in a process of the present invention can further comprise a cover portion and a base portion as set forth above. Preferred embodiments of those portions are also preferred embodiments for use in an analyte detection process.

The following Examples illustrate particular embodiments of the present invention and are not limiting of the claims and specification in any way.

EXAMPLE 1

Construction of Analyte Detection Device

Multiple layers of thin plastic sheets and adhesive tape were used to construct the detection device. The overall thickness of the device was varied by using varying numbers of layers. Such various layers can be adhered to each other using a suitable adhesive. An exemplary and preferred adhesive is double-sided adhesive tape purchased from 3M. The layers of the device were constructed of high density polystyrene sheets (0.006" thick) purchased from American Can.

After adhering a desired number of plastic sheets together, holes were punched through the adhered layers to make a cavity for the separation and detection layers. A clear bottom layer (polycarbonate) was added, the detection and separation layers inserted and a top layer with application site was added to enclose the layers within the device. Polyethylene terephthalate can be used for the top and bottom layers. A schematic diagram of a detection device of the present invention is shown in FIG. 1.

EXAMPLE 2

Effect of HEPES Buffer

A device was prepared as described in EXAMPLE 1 with the addition that a glass fiber filter, used as the separation layer, contained HEPES buffer, potato lectin and Cremophor EL. The glass fiber filter was impregnated with those substances by soaking the cut filters in an aqueous solution of 150 mM HEPES, pH 7.5, 57,600 Units/L potato lectin and 1.3 percent (w/w) Cremophor EL. After soaking, the fibers were removed from the solution and dried in an oven at 50° C. for about 15 minutes.

A synthetic membrane fabricated of nylon (Biodyne A, 0.45 micron pore size, PALL Biosupport, Long, Island, N.Y.) was impregnated with ATP, NAD, hexokinase, glucose-6-phosphate (G-6-P) dehydrogenase, diaphorase and NBT (a tetrazolium salt, Sigma Chem. Co.) and employed as the detection layer. Impregnation was accomplished by soaking the synthetic membrane in an aqueous solution having the following final concentrations:

5.5% (w/w) Tetrazolium indicator (e.g. NBT)
1% (w/w) NAD
4.7% (w/w) ATP
0.7% (w/w) Magnesium Acetate
0.4% (w/w) Bovine Serum Albumin
800 U/mL Hexokinase
800 U/mL Glucose-6-phosphate Dehydrogenase
800 U/mL Diaphorase
3.7% (w/w) HEPES buffer at pH 7.5
2% inactive ingredients The chemicals were obtained from Sigma Chem. Co. The detection matrix was incorporated with chromogenic indicator first. It was dried in a hot air oven at 50° C. for 5 minutes. The dried matrix was then impregnated with the aqueous solution mentioned above containing the buffer, substrates/cofactors and enzymes. The impregnated matrix was dried again at 50° C. for 10 minutes.

The glass fiber filter and impregnated synthetic membrane (detection matrix) were then sandwiched between a plastic base portion having a transparent polycarbonate window and a thermoformed polystyrene cover having an aperture of 0.10 inches in accordance with the procedures set forth in Example 1.

Figure 2:
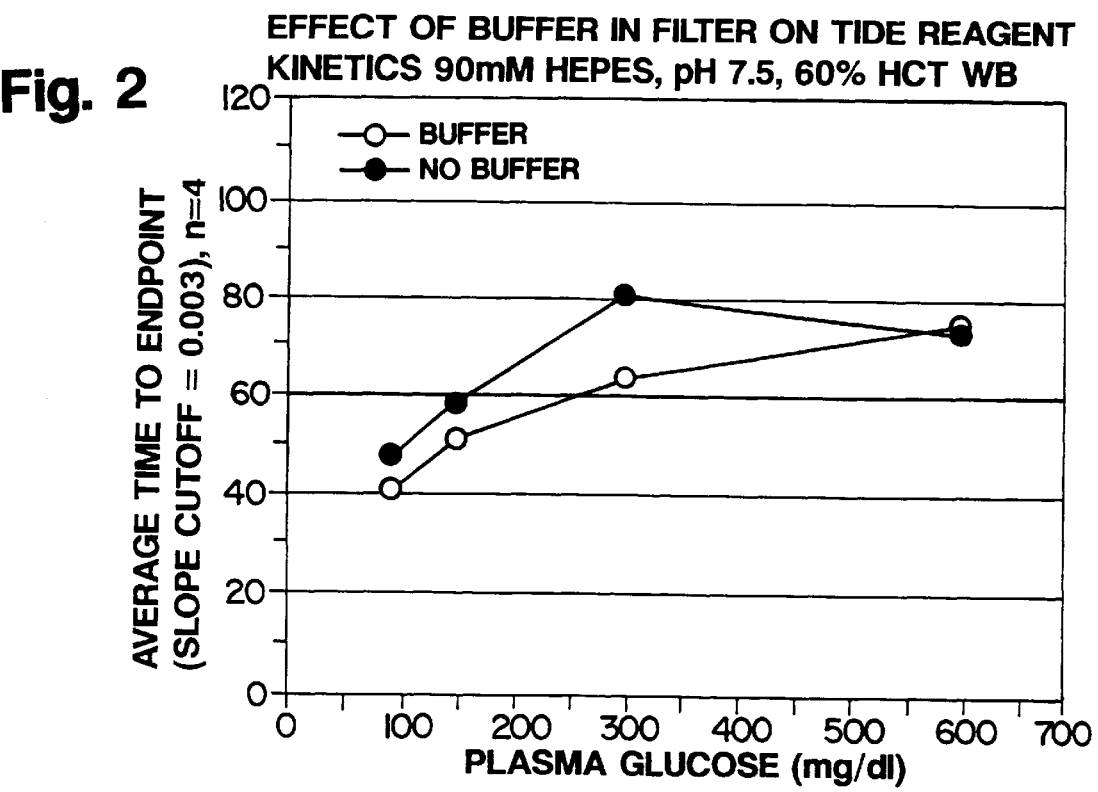
FIG. 2 shows the effects of HEPES buffer in the separation matrix on the determination of glucose in blood having a hematocrit (Hct) of 60%.
Figure 3:
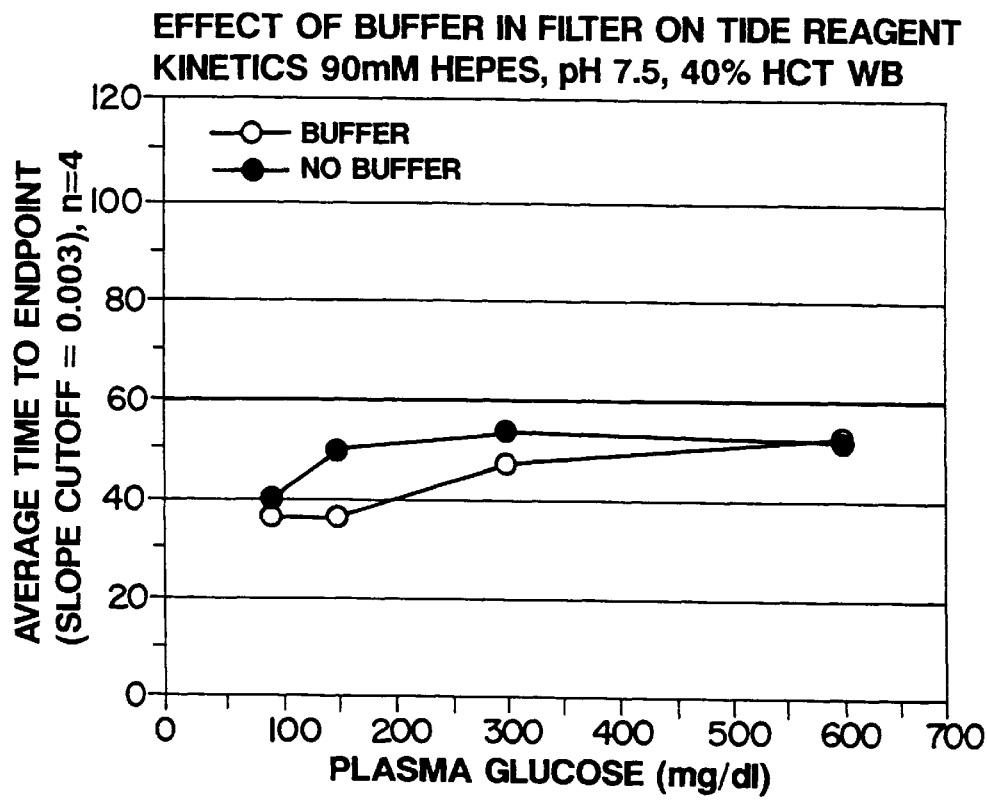
FIG. 3 shows the effects of HEPES buffer in the separation matrix on the determination of glucose in blood having a hematocrit (Hct) of 40%.

Whole blood was applied to the glass fiber filter through the aperture in the polystyrene cover and glucose was detected based on a change in color. The presence of HEPES in separation layer speeded up the end point determination such that the assay could be performed in a time period of less than 80 seconds for both a 40% and a 60% hematocrit whole blood sample (See FIGS. 2 and 3). No benefit was achieved when other buffers, e.g., tris (hydroxymethyl) amino methene (TRIS), TAPSO, MES and saline, were substituted for HEPES.

EXAMPLE 3

Other Analytes

A detection device for other analytes can be prepared using the procedures set forth above. The following impregnation solutions are exemplary of solutions that can be used to impregnate detection matrices for use with the detection of cholesterol, triglyceride and amylase.

Cholesterol:

1.5% (w/w) tetramethylbenzidine hydrochloride indicator dye
4% (w/w) Pipes buffer at pH 7.0
240 U/mL Peroxidase
240 U/mL Cholesterol Esterase
120 U/mL Cholesterol Oxidase
12% inactive ingredients -continued Triglyceride:

1.1% (w/w) Tetrazolium indicator
2.4% (w/w) HEPES buffer at pH 7.5
0.7% (w/w) Magnesium sulfate
2.7% (w/w) ATP
7.1% (w/w) NAD
25000 U/mL Lipase
800 U/mL Lipase
1000 U/mL Glycerol-3-Phosphate Dehydrogenase
500 U/mL Diaphorase
1.5% inactive ingredients Amylase:

17.3% (w/w) p-nitro-maltoheptoside (Genzyme Co.)
16 U/mL Glucoamylase
70 U/mL Alpha-Glucosidase
1.7% (w/w) Pipes, pH 7.0
5 mM Calcium Chloride While the compositions and methods of this invention have been described in terms of preferred embodiments, it will be apparent to those of skill in the art that variations can be applied to the composition, process and in the steps or in the sequence of steps of the process described herein without departing from the concept, spirit and scope of the invention.

What is claimed is:

1. A device for detecting an analyte in a biological fluid, said device comprising:
   a) a separation matrix containing an agglutinating agent and between 70 and 150 millimolar of the buffer 4-(2-hydroxyethyl)-1-piperazine-ethanesulfonic acid (HEPES); and
   b) means for detecting said analyte, which detection means is vertically adjacent to the separation matrix and substantially coincident with the matrix such that said analyte can move from the separation matrix to the means for detecting said analyte;
   wherein said device has a faster endpoint detection speed due to the presence of the HEPES buffer in the separation matrix.

2. The device according to claim 1 wherein said detection means is a membrane containing one or more chemical reagents that interact with the analyte to generate a detectable signal indicative of said analyte presence in said biological fluid.

3. The device according to claim 2 wherein said chemical reagents comprise ATP, NAD, hexokinase, glucose-6-phosphate dehydrogenase, diaphorase and an indicator.

4. The device according to claim 1 wherein said separation matrix is a membrane filter.

5. The device according to claim 4 wherein said membrane filter is a glass fiber filter.

6. The device according to claim 5 wherein said glass fiber filter has a sample application side directed away from said detection means and a reagent side directed toward and adjacent to said detection means, whereby said reagent side has shorter fibers than said application side.

7. The device according to claim 1 wherein said separation matrix also contains an aggregation-promoting substance that promotes aggregation of colloidal particles or cells.

8. The device according to claim 1 wherein said separation matrix also contains a non-hemolytic surfactant.

9. The device according to claim 1 further comprising:
   a) a base portion having a transparent window, which base portion is situated such that said detection means is vertically adjacent to said base portion and at least partially coincident with said transparent window;
   b) a cover portion having an aperture, which cover portion is vertically adjacent to and coincident with said separation matrix.

10. The device according to claim 1 wherein said window is made of polycarbonate.

11. The device of claim 1 in which the amount of HEPES present in the separation matrix is between 80 and 100 millimolar.

12. A device for assaying blood glucose comprising:
   a) a synthetic membrane containing ATP, NAD, hexokinase, glucose-6-phosphate dehydrogenase, diaphorase and an indicator; and
   b) a glass fiber filter vertically adjacent to said synthetic membrane and substantially coincident with said synthetic membrane in which the glass fiber contains an agglutinating agent and the buffer 4-(2-hydroxyethyl)-1-piperazine-ethanesulfonic acid (HEPES);
   wherein said device has a faster endpoint detection speed due to the presence of HEPES buffer in an amount between 70 to 150 millimolar.

13. A process of detecting an analyte in a biological fluid, said process comprising the steps of:
   a) providing a detection device comprising:
      i) a separation matrix containing an agglutinating agent and between 70 and 150 millimolar of the buffer 4-(2-hydroxyethyl)-1-piperazine-ethanesulfonic acid (HEPES); and
      ii) means for detecting said analyte, which detection means, is vertically adjacent to the separation matrix and substantially coincident with that matrix such that said analyte can move from the separation matrix to the means for detecting said analyte;
   b) applying a sample of said biological fluid to said separation matrix; and
   c) determining a reaction between said analyte and said detection means, wherein said process has a faster endpoint detection speed due to the presence of HEPES buffer in the separation matrix.

14. The process according to claim 13 wherein said biological fluid is whole blood.

15. The process according to claim 13 in which HEPES is present in an amount between 80 and 100 millimolar.

* * * * *